US005763184A

United States Patent [19]
Reynolds et al.

[11] Patent Number: 5,763,184
[45] Date of Patent: Jun. 9, 1998

[54] NUCLEOTIDE SEQUENCE VARIATION IN THE ABO GLYCOSYLTRANSFERASE GENE

[75] Inventors: Rebecca Lynne Reynolds; Gabriele Annemarie Zangenberg, both of Alameda, Calif.

[73] Assignee: Roche Molecular Systems, Inc., Branchburg, N.J.

[21] Appl. No.: 763,502

[22] Filed: Dec. 11, 1996

Related U.S. Application Data

[60] Provisional application No. 60/017,117, Jan. 30, 1996.

[51] Int. Cl.$^6$ .......................... C12Q 1/68; C12N 15/00; C07H 21/04
[52] U.S. Cl. .................. 435/6; 435/320.1; 435/810; 536/23.5; 536/24.31; 536/24.33; 935/1; 935/8; 935/77
[58] Field of Search .................. 435/6, 91.1, 91.2, 435/183, 320.1, 810; 536/23.1, 23.5, 24.31, 24.33, 25.3; 935/8, 77, 78, 22

[56] References Cited

U.S. PATENT DOCUMENTS 5,521,301  5/1996  Wallace et al. .................. 536/24.33

OTHER PUBLICATIONS

C. Gassner et al., "ABO Glycosyltransferase Genotyping by Polymerase Chain Reaction Using Sequence–Specific Primers," BLOOD, vol. 88, No. 5, pp. 1852–1856, Sep. 1, 1996.
M. L. Olsson and M. A. Chester, "A Rapid and Simple ABO Genotype Screening Method Using a Novel B/O2 versus A/O2 Discriminating Nucleotide Substitution a tthe ABO Locus," VOX SANG, vol. 69, pp. 2420247, 1995.
W. C. Nierman and D.R> Maglott, eds., ATCC/NIH Repository Catalogue of Human and Mouse DNA Probes and Libraries, Eighth Edition, pp. 1–70, 1994.
Yamamoto et al., May. 1990, "Molecular genetic basis of the histo–blood group ABO system" *Nature* 345:229–233.

Lee and Chang, Sep. 1992, "ABO Genotyping by Polymerase Chain Reaction," *Journal of Forensic Sciences*, 37(5):1269–1275.
Yamamoto et al., Jan. 1990, "Cloning and Characterization of DNA Complementary to Human UDP–GalNAc: Fucα1→2Gal α1→3 GalNAc Tranferase (Histo–blood Group A Transferase) mRNA" *Journal of Biological Chemistry* 265(2):1146–1151.
Ugozzoli and Wallace, 1992, "Application of an Allele–Specific Polymerase Chain Reaction to the Direct Determination of ABO Blood Group Genotypes" *Genomics* 12:670–674.
Johnson and Hopkinson, 1992, "Detection of ABO blood group polymorphism by denaturing gradient gel electrophoresis" *Human Molecular Genetics* 1(5):341–344.
O'Keefe and Dobrovic, 1993, "A Rapid and Reliable PCR Method for Genotyping the ABO Blood Group" *Human Mutation* 2: 67–70.
Stroncek et al., 1995, "Determination of ABO glycosyltransferase genotypes by use of polymerase chain reaction and restriction enzymes" *Transfusion* 35(3):231–240.
Crouse and Vincek, 1995, "Identification of ABO Alleles on Forensic–Type Specimens Using Rapid–ABO Genotyping" *BioTechniques* 18(3):478–483.
Bennett et al., 1995, "Genomic Cloning Of The Human Histo–Blood Group ABO Locus" *Biochemical and Biophysical Research Communications* 206(1):318–325.
Errata, 1995, *Biochemical and Biophysical Research Communications* 211(1):347.
Sigma Molecular Biology Catalog, p. 54, 1989.
Nierman and Maglott, eds., "ATCC/NIH Repository Catalogue ofHuman and Mouse DNA Probes and Libraries," Eighth edition, pp. 1–70, 1994.

*Primary Examiner*—Bradley L. Sisson
*Attorney, Agent, or Firm*—George W. Johnston; Dennis P. Tramaloni; Doug Petry

[57] ABSTRACT

Methods and reagents for determining an individual's genotype at the ABO locus with respect to newly discovered polymorphisms, which facilitates typing tissue for determinign individual identity and has application in the field of forensic science.

13 Claims, No Drawings

NUCLEOTIDE SEQUENCE VARIATION IN THE ABO GLYCOSYLTRANSFERASE GENE

This application claims priority to U.S. provisional application No. 60/017,117, filed Jan. 30, 1996.

BACKGROUND OF THE INVENTION

1. Field of the Invention

The present invention relates to the field of molecular biology and nucleic acid chemistry. More specifically, it relates to methods and reagents for genotyping alleles that encode the glycosyltransferase enzymes which determine the A, B, and H antigen blood groups.

2. Description of Related Art

ABO typing is the oldest conventional serology test performed by forensic scientists. Karl Landsteiner discovered the ABO typing system in 1901 and developed typing methods for use in cases of questioned paternity. The basis for the test is antibody reactivity with A, B, and H antigens which are found on erythrocytes and other types of cells (e.g., epithelial). Forensic scientists use polyclonal antibodies against type A- and type B-antigens in either a direct (whole blood) or indirect (dried stains) agglutination assay to distinguish A, B, O, and AB phenotypes. Usually, no antiserum for the type H-antigen is used; blood from type O individuals does not agglutinate with either type A- or type B-antisera. Without a specific antiserum for the type H-antigen, the AA phenotype cannot be distinguished from the AO phenotype and the BB phenotype cannot be distinguished from the BO phenotype.

The molecular basis of the A, B, and H antigens is known. Antigens A and B are derived from the H oligosaccharide by the action of two glycosyltransferases. Individuals with blood type A express transferase A activity, which transfers N-acetylgalactosamine to the H antigen to form the A antigen. Individuals with blood type B express transferase B activity, which transfers galactose to the H antigen to form the B antigen. Individuals with blood type O lack a functional glycosyltransferase and express only the unmodified H antigen on cell surfaces.

The genetic basis of the ABO glycosyltransferase polymorphism also is known. Yamamoto et al., 1990, *Nature* 345(17):229–233; incorporated herein by reference, report the sequence analysis of cDNAs isolated from individuals of known ABO type. The cDNAs encoding the A and B transferases are 1062 base pairs in length and encode proteins of 353 amino acids. The A and B allele sequences differ from each other at 7 nucleotides and encode proteins which differ at 4 amino acids, which account for the different specificities of the A and B transferases. At position 258 of the coding sequence, the O allele differs from the A and B alleles by a single base pair deletion, which, due to the resulting frameshift in translation, creates a stop codon at nucleotides 349–351. The truncated, 155 amino acid protein encoded by the O allele lacks the functional domain of the transferase.

The invention of the polymerase chain reaction (PCR), a method for amplifying specific sequences of nucleic acids, makes possible the rapid detection of nucleic acids present in a sample in what was previously an undetectably low quantity (see U.S. Pat. Nos. 4,683,195; 4,683,202; and 4,965,188, each of which is incorporated herein by reference). Analysis of amplified nucleic acid sequence can be carried out by a variety of means. For example, detection of ABO genotypes using PCR-amplified nucleic acid has been carried out by restriction enzyme cleavage patterns (see Lee and Chang, 1992, *J. Forensic Sciences, JFSCA* 17(5):1269–1275; and O'Keefe and Dobrovic, 1993, *Human Mutation* 2:67–70, both incorporated herein by reference) and by denaturing gradient gel electrophoresis (see Johnson and Hopkinson, 1992, *Human Mol. Gen.* 1(5):341–344, incorporated herein by reference). Detection of ABO genotypes using allele-specific PCR amplification was described by Ugozzoli and Wallace, 1992, *Genomics* 12:670–674, incorporated herein by reference.

SUMMARY OF INVENTION

The present invention relates to newly discovered nucleotide sequence polymorphisms in the ABO glycosyltransferase gene. The previously defined O type alleles and B type alleles are subdivided based on the variant nucleic acid sequences present at the newly discovered polymorphic sites. The present invention provides methods and reagents for detecting the newly discovered allele sequence variants.

One aspect of the invention relates to a previously unknown intron sequence which occurs upstream of nucleotide position 239 of the coding sequence of the ABO glycosyltransferase gene. The 58 base pair sequence, of which bases 22–58 are newly discovered, is conserved among the ABO alleles, with the exception of the polymorphic sites at positions 29, 32, and 33. A single base pair change at the polymorphic site at nucleotide position 29 is found in a common subtype of the O allele. A single base pair change at the polymorphic site at nucleotide position 33 distinguishes a less common subtype of the O allele. A single base pair change at the polymorphic site at nucleotide position 32 distinguishes a subtype of the B allele.

Another aspect of the invention relates to isolated oligonucleotides which comprise a nucleotide sequence at least about 10 nucleotides in length, wherein said nucleotide sequence is contained in the newly discovered ABO glycosyltransferase gene intron sequence provided herein. These oligonucleotides are useful as amplification primers, detection probes, and positive control sequences which are added to reactions to provide a known target sequence. For use as a positive control sequence, the oligonucleotide is preferably contained in a DNA vector such as a plasmid.

Another aspect of the invention relates to isolated oligonucleotides which are exactly or substantially complementary to either strand of a newly discovered variant ABO glycosyltransferase gene in a region of the gene which encompasses a newly discovered polymorphic site, and are exactly complementary at the polymorphic site. These oligonucleotides are useful as sequence-specific amplification primers, sequence-specific detection probes, and positive control sequences which are added to reactions to provide a known target sequence. Used as a detection probe, the oligonucleotide enables the detection of a variant allele sequence by nucleic acid hybridization. Used as an amplification primer, the oligonucleotide enables the sequence-specific amplification of nucleic acid from a variant allele. For use in sequence-specific amplification or detection, the oligonucleotide preferably is about 15 to about 35 nucleotides in length.

Another aspect of the invention relates to methods for detecting allelic sequence variants of the ABO glycosyltransferase gene from a sample containing nucleic acid obtained from an individual, wherein the methods comprise detecting the base pair present at one or more of the newly discovered polymorphic sites. In a preferred embodiment of the invention, the base pair present at a polymorphic site is identified by hybridizing the sample nucleic acid with an oligonucleotide which is exactly or substantially complementary to either strand of a newly discovered variant ABO glycosyltransferase gene in a region of the gene which encompasses the polymorphic site, and is exactly complementary at the polymorphic site to the variant sequence. Hybridization is carried out under sufficiently stringent conditions such that the oligonucleotide binds to the nucleic acid to form stable hybrid duplexes only if the sample nucleic acid contains the variant target allele sequence. The presence of the variant allele sequence in the sample is determined by detecting the presence or absence of stable hybrid duplexes formed between the oligonucleotide and the sample nucleic acid. In a preferred embodiment of the invention, the detection of allelic sequence variants is carried out in order to determine the genotype of an individual at the ABO glycosyltransferase locus.

The presence of stable hybrid duplexes can be carried out by any of the means known in the art. Various detection assay formats are well known which utilize detectable labels bound to either the target nucleic acid or to the oligonucleotide probe to enable detection of hybrid duplexes. Typically, hybridization duplexes are separated from unhybridized nucleic acid and the labels bound to the duplexes are then detected. Alternatively, an amplification reaction can be carried out using the oligonucleotide as one of the primers under conditions such that amplification occurs only if a stable hybridization duplex is present. The presence of amplified DNA serves as an indicator of the presence of stable hybrid duplexes and, consequently, the presence of the target sequence in the sample.

If sufficient nucleic acid is present in the sample, detection by oligonucleotide probe hybridization may be carried out without prior amplification of the target sequence. However, in a preferred embodiment of the invention, the sample contains amplified nucleic acids, wherein a region of the ABO glycosyltransferase gene which encompasses the probe hybridization region is amplified. Any of the known methods for increasing the copy number of a region of nucleic acid in vitro can be used to amplify the nucleic acid. The polymerase chain reaction (PCR) is the preferred amplification method. Another aspect of the invention is a method for amplifying a region of the ABO glycosyltransferase gene which comprises carrying out an amplification reaction using an oligonucleotide primer which hybridizes to the newly-discovered intron sequence provided herein.

Another aspect of the invention relates to kits useful for determining the ABO genotype of an individual. These kits take a variety of forms and comprise one or more probes and, in one embodiment, comprise a panel of probes sufficient to determine the ABO genotype. The kits can also comprise one or more amplification reagents, e.g., primers, polymerase, buffers, and nucleoside triphosphates.

Another aspect of the invention relates to forensic methods to determine the probable origin of a biological sample. The discovery of additional alleles substantially improves the discriminational power of ABO DNA typing methodology and will have an important impact on forensic methodology.

DETAILED DESCRIPTION OF THE INVENTION

To aid in understanding the invention, several terms are defined below.

The terms "ABO glycosyltransferase gene", "ABO glycosyltransferase locus", "ABO gene", and "ABO locus" refer to the genomic nucleic acid sequence that includes the translated sequences that code for the ABO glycosyltransferase protein and the untranslated intervening sequences. The nucleotide sequence of the gene, as used herein, encompasses both coding regions, referred to as exons, and intervening, non-coding regions, referred to as introns.

The term "alleles" refers to variants of the nucleotide sequence of a gene.

An ABO glycosyltransferase gene "A" allele refers to sequence variants that encode a protein which possesses N-acetylgalactosaminosyl transferase activity. A "B" allele refers to sequence variants that encode a protein which possesses galactosyl transferase activity. An "O" allele refers to sequence variants of the ABO gene that encode a protein which lacks glycosyltransferase activity. An O allele contains a single base pair deletion at position 258 relative to the A and B alleles, which, due to the resulting translation frameshift, creates a stop codon at nucleotides 349–351. The truncated, 155 amino acid protein encoded by the O allele lacks the functional domain of the transferase.

The term "genotype" refers to a description of the alleles of a gene contained in an individual or a sample.

The terms "polymorphic" and "polymorphism", as used herein, refer to the condition in which two or more variants of a specific genomic sequence can be found in a population. The polymorphic region or polymorphic site refers to that region of the nucleic acid where a polymorphism occurs.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Oligonucleotides can be prepared by any suitable method, including, for example, cloning and restriction of appropriate sequences and direct chemical synthesis by a method such as the phosphotriester method of Narang et al., 1979, Meth. Enzymol. 68:90–99; the phosphodiester method of Brown et al., 1979, Meth. Enzymol. 68:109–151; the diethylphosphoramidite method of Beaucage et al., 1981, Tetrahedron Lett. 22:1859–1862; and the solid support method of U.S. Pat. No. 4,458,066, each incorporated herein by reference. A review of synthesis methods is provided in Goodchild, 1990, Bioconjugate Chemistry 1(3):165–187, incorporated herein by reference. Methods for incorporating an oligonucleotide into a DNA vector, such as for use as a positive control target sequence, are well known in the art and described in references cited herein.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch, wherein the total number of mismatched nucleotides is no more than about 3. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. Computer software for calculating duplex stability is commercially available from National Biosciences, Inc. (Plymouth,Minn.); the OLIGO version 5 reference manual is incorporated herein by reference.

Stringent, sequence-specific hybridization conditions, under which an oligonucleotide will hybridize only to the exactly complementary target sequence, are well known in the art (see, e.g., Sambrook et al., 1989, *Molecular Cloning—A Laboratory Manual*, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

The term "probe" refers to an oligonucleotide which is capable of selectively hybridizing to a target nucleic acid under suitable conditions. The probe will contain a "hybridizing region" exactly or substantially complementary to the target sequence, and will be exactly complementary to the target sequence at a polymorphic site. A hybridization assay carried out using the probe under sufficiently stringent hybridization conditions enables the selective detection of a specific target sequence. For use in a hybridization assay for the discrimination of single nucleotide differences in sequence, the probe hybridizing region is preferably from about 15 to about 35 nucleotides in length. One of skill in the art will recognize that, in general, the exact complement of a given probe is equally useful as a probe. A probe oligonucleotide can either consist entirely of the hybridizing region or can contain additional features which allow for the detection or immobilization of the probe, but which do not significantly alter the hybridization characteristics of the hybridizing region. For example, the probe hybridizing region may be bound to a poly-T "tail", which is used to immobilize the probe to a solid support for use in the reverse dot-blot assay.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer will contain a "hybridizing region" exactly or substantially complementary to the target sequence, and will be exactly complementary to the target sequence at a polymorphic site. An amplification carried out using the primer in which primer extension is carried out under sufficiently stringent hybridization conditions allows the selective amplification of a specific target sequence. For use in sequence-specific amplifications for the discrimination of single nucleotide changes in sequence, the primer hybridizing region is preferably from about 15 to about 35 nucleotides in length. Because primer extension occurs at the 3' end of the oligonucleotide, the polymorphic site preferably is situated at the 3' end of the primer to facilitate sequence discrimination. A primer oligonucleotide can either consist entirely of the hybridizing region or can contain additional features which allow for the detection, immobilization, or manipulation of the amplified product, but which do not alter the basic property of the primer, that of acting as a point of initiation of DNA synthesis. For example, to facilitate cloning of the amplified product, a short nucleic acid sequence which contains a restriction enzyme cleavage site can be bound to the 5' end of the primer.

The term "target region" refers to a region of a nucleic acid which is to be analyzed and usually includes a polymorphic region.

Conventional techniques of molecular biology and nucleic acid chemistry, which are within the skill of the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); and a series, Methods in Enzymology (Academic Press, Inc.), all of which are incorporated herein by reference. All patents, patent applications, and publications mentioned herein, both supra and infra, are incorporated herein by reference.

ABO Glycosyltransferase Gene Nucleotide Sequence

The nucleotide sequence of a region of the ABO glycosyltransferase gene is provided as SEQ ID NO: 1 and is shown in a 5' to 3' orientation in Table 1, below. The base codes used in SEQ ID NO: 1 are as follows: A=adenine; C=cytosine; G=guanine; T=thymine; R=adenine or guanine; Y=cytosine or thymine. The region consisting of positions 1–58 of SEQ ID NO: 1, which is shown in italics, is an intronic region. Positions 59–161 of SEQ ID NO: 1 corresponds to nucleotides 239–341 of the full coding sequence of the O allele, and nucleotides 239–257 and 259–342 of full coding sequence of the A and B alleles. The polymorphic sites within the O allele ("R" at positions 29, 32, and 113; "Y" at position 33) are shown underlined. The intronic sequence consisting of positions 22–58, shown in bold, is newly discovered.

Although only one strand of the O allele nucleic acid is shown in Table 1, those of skill in the art will recognize that SEQ ID NO: 1 identifies a region of double-stranded genomic nucleic acid, and that the sequences of both strands are fully specified by the sequence information provided. For notational convenience, complementary base pairs of the double stranded genomic DNA are shown herein separated by a colon. The first nucleotide of a complementary pair refers to the nucleotide present in the single strand shown in Table 1.

TABLE 1

Partial Nucleotide Sequence of the ABO Glycosyltransferase Gene (SEQ ID NO: 1)

| | | | | | |
|---|---|---|---|---|---|
| CATGTGGGTG | GCACCCTGCC | AGCTCCATRT | GRYCGCACGC | CTCTCTCCAT | 50 |
| GTGCAGTAGG | AAGGATGTCC | TCGTGGTACC | CCTTGGCTGG | CTCCCATTGT | 100 |
| CTGGGAGGGC | ACRTTCAACA | TCGACATCCT | CAACGAGCAG | TTCAGGCTCC | 150 |
| AGAACACCAC | C | | | | 161 |

As noted above, the O allele contains a single base pair deletion relative to the coding sequence of the A and B alleles at nucleotide position 258 of the coding sequence. The A and B alleles contain an additional G:C base pair between positions 77 and 78 of SEQ ID NO: 1, which corresponds to nucleotide 258 of the coding sequence of the A and B alleles. Consequently, bases 78–161 of SEQ ID NO: 1 correspond to nucleotide positions 258–341 of the coding sequence of the O alleles and to nucleotide positions 259–342 of the coding sequence of the A and B alleles.

Seven nucleotide sequence variants (alleles) of the ABO glycosyltransferase gene have been observed which are distinguished by the particular base pairs present at the polymorphic sites within SEQ ID NO: 1. These seven alleles are designated herein as $O_1$, $O_2$, $O_3$, $O_4$, A, $B_1$, and $B_2$. The allele designations used herein are defined in Table 2, below, in terms of the particular base pairs present at the polymorphic sites at positions 29, 32, 33, and 113, and the presence or absence of an additional G:C base pair between positions 77 and 78 of SEQ ID NO: 1 (denoted by "G:C?" in Table 2). The positions of the polymorphic sites are numbered in reference to SEQ ID NO: 1.

TABLE 2

ABO Glycosyltransferase Alleles

| Allele | Position 29 | Position 32 | Position 33 | G:C? | Position 113 |
|---|---|---|---|---|---|
| $O_1$ | A:T | A:T | C:G | No | G:C |
| $O_2$ | G:C | A:T | C:G | No | A:T |
| $O_3$ | G:C | A:T | C:G | No | G:C |
| $O_4$ | A:T | A:T | T:A | No | G:C |
| A | G:C | A:T | C:G | Yes | A:T |
| $B_1$ | G:C | A:T | C:G | Yes | G:C |
| $B_2$ | G:C | G:C | C:G | Yes | G:C |

The A:T/G:C polymorphism present in the intronic sequence at position 29 of SEQ ID NO: 1 subdivides the O alleles into two groups: the $O_1$ and $O_4$ alleles, which both contain an A:T base pair at position 29, and the $O_2$ and $O_3$ alleles, which both contain a G:C base pair at position 29. Thus, regions of SEQ ID NO: 1 which encompass position 29 provide novel nucleic acid target sequences which can be used to distinguish among O alleles. The corresponding position in the intronic sequences of the A and B alleles is not polymorphic and contains a G:C base pair.

The A:T/G:C polymorphism present in the intronic sequence at position 32 of SEQ ID NO: 1 subdivides the B alleles into the $B_1$ (A:T) and $B_2$ (G:C) alleles. Thus, regions of SEQ ID NO: 1 which encompass position 32 provide novel nucleic acid target sequences which can be used to distinguish between B alleles. The corresponding position in the intronic sequences of the A and O alleles is not polymorphic and contains an A:T base pair.

The C:G/T:A polymorphism present in the intronic sequence at position 33 of SEQ ID NO: 1 subdivides the O alleles into two groups: the $O_1$, $O_2$, and $O_3$ alleles, which all contain an C:G base pair at position 33, and the $O_4$, which contains a T:A base pair at position 33. Thus, regions of SEQ ID NO: 1 which encompass position 33 provide novel nucleic acid target sequences which can be used to identify the $O_4$ allele. The corresponding position in the intronic sequences of the A and B alleles is not polymorphic and contains an C:G base pair.

The intronic sequences at positions 1–27 and 34–58 of SEQ ID NO: 1 are conserved among ABO alleles. These regions provided novel nucleic acid target sequences for the detection or amplification of the ABO glycosyltransferase gene regardless of allele type.

The G:C/A:T polymorphism present in the coding sequence at position 113 of SEQ ID NO: 1 distinguishes the $O_2$ allele from the $O_1$, $O_3$, and $O_4$ alleles, and also distinguishes A from B alleles. $O_1$, $O_3$, and $O_4$ alleles contain a G:C base pair at position 113, and B alleles contain a G:C base pair at the corresponding position. $O_2$ alleles contain an A:T base pair at position 113, and A alleles contain an A:T base pair at the corresponding position. Thus, regions which encompass position 113 can be used to distinguish A and $O_2$ alleles, which both contain an A:T base pair, from B, $O_1$, $O_3$, and $O_4$ alleles, which all contain a G:C base pair.

In the methods of the present invention, allelic sequence variants are identified by detecting the base pairs present at one or more of the polymorphic sites described above. The base pairs present can be determined by sequencing a region of the gene encompassing one or more polymorphic sites, or by any means which discriminates among sequence variations. For example, changes in the mobility measured by gel electrophoresis can be used to distinguish allelic sequences. The preferred hybridization detection methods are based on the difference in stability of hybridization duplexes, formed between the allele nucleic acid and primer or probe oligonucleotides, which differ in the degree of complementarity. Under sufficiently stringent hybridization conditions, only duplexes formed between the probe or primer oligonucleotide and target sequences will be stable. The presence of stable hybridization duplexes can be detected by any of a number of well known methods, such as by the use of labeled probes or by the ability to carry out the primer extension necessary for an amplification reaction.

In one embodiment of the present invention, the nucleotide present at a particular polymorphic site is identified by hybridization under sequence-specific hybridization conditions with an oligonucleotide exactly complementary to a target region of SEQ ID NO: 1, or the complement of SEQ ID NO: 1, encompassing the polymorphic site. Under sequence-specific hybridization conditions, an oligonucleotide exactly complementary to a variant allele in a region which encompasses a polymorphic site will hybridize only to the variant allele. Thus, oligonucleotides, preferably from about 15 to about 35 nucleotides in length, which are exactly complementary to an allele sequence in a region which encompasses a polymorphic site are within the scope of the invention.

In an alternative embodiment of the invention, the nucleotide present at a particular polymorphic site is identified by hybridization under sufficiently stringent hybridization conditions with an oligonucleotide substantially complementary, i.e., containing no more than about 3 mismatches, to a target region of SEQ ID NO: 1, or the complement of SEQ ID NO: 1, encompassing the polymorphic site, and which is exactly complementary to the target sequence at any polymorphic sites. Because mismatches which occur at non-polymorphic sites are mismatches with all allele sequences, the difference in the number of mismatches in a duplex formed with the target sequence and in a duplex formed with the corresponding non-target allele sequence is the same as when an oligonucleotide exactly complementary to the target sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, an oligonucleotide substantially complementary to a variant allele in a region which encompasses a polymorphic site, which is exactly complementary to the target sequence at any polymorphic sites, will hybridize only to the variant allele. Thus, oligonucleotides, preferably from about 15 to about 35 nucleotides in length, which are substantially complementary to an allele sequence in a region which encompasses a polymorphic site, and are exactly complementary to the allele sequence at any polymorphic sites, are within the scope of the invention.

The use of substantially, rather than exactly, complementary oligonucleotides may be desirable in assay formats in which optimization of hybridization conditions is limited. For example, in a typical immobilized probe assay format, as described below, multiple probes are immobilized on a single solid support. Hybridizations are carried out simultaneously by contacting the solid support with a solution containing target DNA. As the individual hybridizations are carried out under identical conditions, the hybridization conditions cannot be separately optimized for each probe. Thus, probe sequences are selected such that the probe/target duplex stabilities are similar under the same hybridization conditions. Because mismatches decrease the stability of the probe/target hybridization duplex, and thus alter the hybridization conditions needed to provide sufficient stringency for the assay, the incorporation of mismatches into the design of a probe can be used to adjust duplex stability when the assay format precludes adjusting the hybridization conditions. The effect of a particular introduced mismatch on duplex stability is well known, and the duplex stability can be routinely both estimated and empirically determined, as described above.

Preferred Oligonucleotides Probes

The polymorphisms to be detected consist of single base pair differences. Single base differences in sequence can be detected by differential hybridization of oligonucleotide probes. The probe hybridizing sequence and sequence-specific hybridization conditions are selected such that a single mismatch at the polymorphic site destabilizes the hybridization duplex sufficiently so that it is effectively not formed. Thus, in the methods of the present invention, the nucleotide present at a particular polymorphic site is identified by hybridization under sufficiently stringent hybridization conditions with an oligonucleotide probe containing a hybridizing region substantially complementary to a target region of SEQ ID NO: 1, or the complement of SEQ ID NO: 1, wherein the target region encompasses the polymorphic site, and exactly complementary at the polymorphic site. The hybridization conditions depend on the exact size and sequence of the probe, and can be selected empirically using the guidance provided herein and in the prior art. The use of oligonucleotide probes to detect single base pair differences in sequence is described in Conner et al., 1983, Proc. Natl. Acad. Sci. USA 80:278–282, which is incorporated herein by reference.

Because of the proximity of the polymorphic sites at positions 29, 32, and 33, probes which encompass positions 29–33 can be used to detect the pattern of base pairs present at positions 29, 32, and 33. As seen in Table 2, all seven alleles contain one of four distinct variant sequences in the region from position 29 to position 33. Thus, using one probe to detect each possible combination of base pairs, four probes are sufficient to positively detect each allele sequence within the region encompassing positions 29–33. An example set of four probes sufficient to determine the base pair present at positions 29, 32, and 33 in each allele is provided in the examples.

The proportional change in stability between a perfectly matched and a single-base mismatched hybridization duplex depends on the length of the hybridized oligonucleotides. Duplexes formed with shorter probes sequences are destabilized proportionally more by the presence of a mismatch. In practice, oligonucleotides between about 15 and about 35 nucleotides in length are preferred for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. Preferably, for discrimination of a single base pair change in target sequence, the probe sequence is selected which hybridizes to the target sequence such that the polymorphic site occurs in the interior region of the probe.

The above criteria for selecting a probe sequence which hybridizes to SEQ ID NO: 1 apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

Preferred Oligonucleotide Amplification Primers

In a preferred embodiment of the invention, the process for determining the ABO genotype comprises amplifying a nucleic acid sequence from the ABO gene which contains polymorphic sites, identifying the nucleotide present at each polymorphic site using oligonucleotide probes under sequence-specific hybridization conditions, and inferring the ABO genotype from the pattern of binding of the probes to the amplified target sequence. In this embodiment, amplification is carried out to provide sufficient nucleic acid for analysis by probe hybridization. Thus, primers are designed such that a region of the ABO gene encompassing the polymorphic site(s) is amplified regardless of the allele present in the sample. Allele-independent amplification is achieved using primers which hybridize to conserved regions of the ABO gene.

In an alternative embodiment of the present invention, sequence-specific amplification is carried out using a primer which hybridizes to a region of the ABO gene which encompasses a polymorphic site. Amplification conditions are chosen such that amplification occurs only if the target allele sequence is present in the sample. In this manner, the nucleotide present is identified by the presence or absence of amplification product; no additional sequence analysis of the amplified product is required. The detection of amplified product can be carried out by any of the methods well known in the art, such as analysis by gel electrophoresis.

The hybridization specificity of the primers is a critical property of the primers which enables sequence-specific amplification. In general, the 3' end, which is the primer extension site, is more critical to the specificity of the primer because a mismatch at the 3' end can destabilize the 3' end and interfere with primer extension even though the 5' portion of the primer is hybridized to the target sequence. Thus, for the discrimination of single nucleotide changes in sequence, it is preferable that the primer sequence hybridize to the target sequence such that the polymorphic site hybridizes at or near the 3' end of the primer. Allele-specific amplification and the effects of primer mismatches are described in Ugozzoli et al., 1991, *Methods: A Companion to Methods in Enzymology* 2:42–48; Kwok et al., 1990, *Nucleic Acids Research* 18:999–1005; and Kwok et al., 1994, *PCR Methods and Applications* 3:S:39–47, each incorporated herein by reference.

An additional sequence containing a restriction enzyme cleavage site (restriction sites) can be added to the 5' end of a primer without affecting the ability of the primer to be extended. The restriction site, which is incorporated into the amplified product, facilitates cloning the amplified product for use in, for example, sequencing (see U.S. Pat. No. 4,683,195). Typically, sequences between about 2 and about 10 bases in length which are not complementary to the target sequence can be added to the 5' end of the primer hybridizing region without significantly altering the ability of the primers to catalyze the specific amplification of ABO alleles. The exact length and sequence of the added 5' terminal sequences will be determined by the restriction site desired. One of skill in the art will realize that minor optimization of the amplification conditions may be necessary depending on the sequence added. However, one of skill in the art will also recognize that, for use in the present methods, a primer lengthened with an additional sequence at the 5' end which contains a restriction enzyme cleavage site is essentially equivalent to the unlengthened primer.

Amplification and Detection Methods

Any type of tissue containing ABO nucleic acid may be used for determining the ABO genotype of an individual. Simple and rapid methods of preparing samples for PCR are described in Higuchi, 1989, in *PCR Technology* (Erlich ed., Stockton Press, New York). A preferred procedure is the Chelex extraction method described in Singer-Sam et al., 1989, *Amplifications* 3:11, and Walsh et al., 1991, *BioTechniques* 10(4):506–513, both of which are incorporated herein by reference. Because the genotyping methods of the present invention can utilize amplified nucleic acids, and because the PCR technique can amplify extremely small quantities of nucleic acid, the ABO genotype can be determined even from samples containing only a few copies of the ABO gene. For instance, even the root end of a single hair contains enough DNA for purposes of the present invention, as evidenced by the DQalpha DNA typing methods described by Higuchi et al., 1988, *Nature* 332:543–546, incorporated herein by reference. The feasibility of using single sperm for DNA typing is demonstrated in Li et al., 1988, *Nature* 335:441–417.

The polymerase chain reaction (PCR) amplification process is well known in the art and described in U.S. Pat. Nos. 4,683,195; 4,683,202; and 4,965,188, each incorporated herein by reference. Commercial vendors, such as Perkin Elmer (Norwalk, Conn.) market PCR reagents and publish PCR protocols. A summary of PCR is provided below.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

Due to the enormous amplification possible with the PCR process, low levels of DNA contamination from samples with high DNA levels, positive control templates, or from previous amplifications can result in PCR product, even in the absence of purposefully added template DNA. Laboratory equipment and techniques which will minimize cross contamination are discussed in Kwok and Higuchi, 1989, *Nature* 339:237–238 and Kwok and Orrego, in: Innis et al. eds., 1990, *PCR Protocols: A Guide to Methods and Applications*, Academic Press, Inc., San Diego, Calif., which are incorporated herein by reference. Enzymatic methods to reduce the problem of contamination of a PCR by the amplified nucleic acid from previous reactions are described in PCT patent publication Serial No. US 91/05210 and U.S. Pat. Nos. 5,418,149 and 5,035,996, each incorporated herein by reference.

Amplification reaction mixtures are typically assembled at room temperature, well below the temperature needed to insure primer hybridization specificity. Non-specific amplification may result because at room temperature the primers may bind non-specifically to other, only partially complementary nucleic acid sequences, and initiate the synthesis of undesired nucleic acid sequences. These newly synthesized, undesired sequences can compete with the desired target sequence during the amplification reaction and can significantly decrease the amplification efficiency of the desired sequence. Non-specific amplification can be reduced using a "hot-start" wherein primer extension is prevented until the temperature is raised sufficiently to provide the necessary hybridization specificity.

In one hot-start method, one or more reagents are withheld from the reaction mixture until the temperature is raised sufficiently to provide the necessary hybridization specificity. Hot-start methods which use a heat labile material, such as wax, to separate or sequester reaction components are described in U.S. Pat. No. 5,411,876 and Chou et al., 1992, *Nucleic Acids Research* 20(7):1717–1723, both incorporated herein by reference. In another hot-start method, a reversibly inactivated DNA polymerase is used which does not catalyze primer extension until activated by a high temperature incubation prior to, or as the first step of, the amplification (see copending U.S. patent application Ser. No. 60/002,673, filed Aug. 25, 1995. Non-specific amplification also can be reduced by enzymatically degrading extension products formed prior to the initial high-temperature step of the amplification, as described in U.S. Pat. No. 5,418,149, which is incorporated herein by reference.

Although the polymerase chain reaction is the preferred amplification method, amplification of target sequences in a sample may be accomplished by any known method, such as ligase chain reaction (Wu and Wallace 1988, *Genomics* 4:560–569, incorporated herein by reference), the TAS amplification system (Kwoh et al, 1989, *Proc. Natl. Acad. Sci. USA* 86:1173–1177, incorporated herein by reference), and self-sustained sequence replication (Guatelli et al., 1990, *Proc. Natl. Acad. Sci. USA* 87:1874–1878; and WO 92/08800; both incorporated herein by reference), each of which provides sufficient amplification so that the target sequence can be detected. Alternatively, methods that amplify the probe to detectable levels can be used, such as QB-replicase amplification (Kramer and Lizardi, 1989, *Nature* 339:401–402, and Lomeli et al., 1989, *Clin. Chem.* 35:1826–1831, both of which are incorporated herein by reference). A review of known amplification methods is provided in Abramson and Myers, 1993, *Current Opinion in Biotechnology* 4:41–47, incorporated herein by reference.

The ABO allele(s) present in a sample can be identified by sequence-specific amplification or by first amplifying a region of the allele and then identifying the nucleotide sequence present by analyzing the sequence of the amplified region. Sequence analysis can be carried out by any means which can discriminate the sequence variations found in the amplified nucleic acid. Sequence analysis is preferably carried out by hybridization with oligonucleotide probes of the present invention, although other methods can be used, such as direct sequencing of the amplified nucleic acid and detection of changes in the mobility measured by gel electrophoresis. Suitable assay formats for detecting hybrids formed between probes and target nucleic acid sequences in a sample are known in the art and include the dot-blot format and immobilized probe assay formats, such as the reverse dot-blot assay. Dot blot and reverse dot blot assay formats are described in U.S. Pat. Nos. 5,310,893; 5,451,512; and 5,468,613, each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA.

Another suitable assay method, referred to as a 5'-nuclease assay, is described in U.S. Pat. No. 5,210,015 and Holland et al., 1991, *Proc. Natl. Acad. Sci. USA* 88:7276–7280, both incorporated herein by reference, in which the labeled detection probes are added during the PCR amplification process. The probes are modified so as to prevent the probes from acting as primers for DNA synthesis. Any probe which hybridizes to target DNA during each synthesis step, i.e., during primer extension, is degraded by the 5' to 3' exonuclease activity of the DNA polymerase, e.g., Taq DNA polymerase. The degradation product from the probe is then detected. Thus, the presence of probe degradation product indicates both that hybridization between probe and target DNA occurred and that the amplification reaction occurred. Oligonucleotides which have been modified to function as probes in the methods of the '015 patent are within the scope of the present invention. Methods for detecting the degradation of probe which occurs concomitant with amplification are described in the '015 patent and U.S. Pat. Nos. 5,491,063 and 5,571,673 now allowed, both incorporated herein by reference.

The assay formats described above typically utilize labeled oligonucleotides to facilitate detection of the hybrid duplexes. Oligonucleotides can be labeled by incorporating a label detectable by spectroscopic, photochemical, biochemical, immunochemical, or chemical means. Useful labels include $^{32}$P, fluorescent dyes, electron-dense reagents, enzymes (as commonly used in ELISAS), biotin, or haptens and proteins for which antisera or monoclonal antibodies are available. Labeled oligonucleotides of the invention can be synthesized and labeled using the techniques described above for synthesizing oligonucleotides.

In a preferred embodiment of the invention, a dot-blot assay is carried out using probes labeled with biotin, as described in Levenson and Chang, 1989, in *PCR Protocols: A Guide to Methods and Applications* (Innis et al., eds., Academic Press, San Diego), pages 99–112, incorporated herein by reference. Following hybridization of the immobilized target DNA with the biotinylated probes under sequence-specific conditions, probes which remain bound are detected by first binding the biotin to avidin-horseradish peroxidase (A-HRP) or streptavidin-horseradish peroxidase (SA-HRP), which is then detected by carrying out a reaction in which the HRP catalyzes a color change of a chromogen.

In the alternative methods of ABO typing based on sequence-specific amplification, identification of the presence of a specific sequence requires only detection of the presence or absence of amplified target sequences. Methods for the detection of amplified target sequences are well known in the art. For example, gel electrophoresis (see Sambrook et al., 1989, supra.) and the probe hybridization assays described above have been used widely to detect the presence of nucleic acids.

An alternative method for detecting amplification of nucleic acid by monitoring the increase in the total amount of double-stranded DNA in the reaction mixture is described in Higuchi et al., 1992, *Bio/Technology* 10:413–417; Higuchi et al., 1993, *Bio/Technology* 11:1026–1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence.

Whatever the method for determining which oligonucleotides of the invention selectively hybridize to ABO allelic sequences in a sample, the central feature of the typing method involves the identification of the ABO alleles present in the sample by detecting the variant sequences present. The specific application will determine which probes are used in a panel. For instance, if only the presence or absence of a particular allele is of interest, a single probe specific for the particular allele may be adequate.

It will be clear to one of skill in the art that sets of sequence-specific probes can be chosen which identify classes of alleles, rather than uniquely identify each allele. In some applications, identification of all alleles is not necessary. For example, the methods of the present invention can be used to detect allelic variants not distinguishable by serological methods. However, in applications wherein only the serological type is to be detected, it may be desirable to use a set of probes which distinguishes between the sets of alleles which correspond to each serological type, but does not distinguish between the alleles within each serological type. Use of such a set of probes can allow a significant reduction in the number of probes required.

DNA typing of ABO alleles by the present methods is useful for many different purposes including blood typing for blood banks and for individual identification. For example, DNA typing methods now play a significant role in the important area of individual identification, whether for solving crimes, as when the identity of a criminal or victim is established by linking an individual with evidence left at the scene of a crime, or for solving other issues of a non-criminal nature, as when biological material is used to determine the maternity or paternity of an individual (see, for example, Reynolds and Sensabaugh 1991, *Anal. Chem.* 6:2–15). The discriminational power of a DNA genotyping assay depends on the number and frequency of alleles found at a locus. The discovery of an additional ABO locus polymorphism which subdivides the previously defined O alleles, along with the methods and reagents provided herein for detecting the newly discovered alleles, substantially improves the discriminational power of an ABO DNA typing assay and thereby improves its utility for individual identification.

The present invention also relates to kits, multicontainer units comprising useful components for practicing the present method. A useful kit can contain oligonucleotide probes specific for the ABO alleles. In some cases, the probes may be fixed to an appropriate support membrane. The kit can also contain primers for PCR amplification, as such primers are useful in the preferred embodiment of the invention. These primers will amplify a polymorphic region of the ABO locus. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

ABO Amplification

The amplification of a region of the ABO glycosyltransferase gene from human genomic DNA samples is described below.

Amplification Primers

Amplification of a region of the ABO glycosyltransferase gene corresponding to nucleotides 2–161 of SEQ ID NO: 1, which encompasses the polymorphic sites described herein, was carried out using the primers shown below.

GZ23   SEQ ID NO: 2   5'-ATGTGGGTGGCACCCTGC

GZ21   SEQ ID NO: 3   5'-GGTGGTGTTCTGGAGCCTGAA

The upstream primer, GZ23 (SEQ ID NO: 2), hybridizes to a region of the intron at positions 2–19 of SEQ ID NO: 1. The downstream primer, GZ21 (SEQ ID NO: 3), hybridizes to a region of the coding sequence at positions 141–161 of SEQ ID NO: 1. Together, these primers catalyze the amplification of a 160 nucleotide product from the O alleles and the corresponding 161 nucleotide product from the A and B alleles. Both primer hybridization regions are conserved among ABO alleles. Thus, the primers enable amplification of a nucleic acid sequence from each ABO allele under the same conditions.

Amplification

Each PCR amplification was carried out in a total reaction volume of 100 µl. The final reagent concentrations were as follows:

2 ng purified human genomic DNA 200 nM each primer

200 µM of each dNTP 50 mM KCl 10 mM Tris-HCl, pH 8.3

2.5 mM MgCl$_2$.

2.5 units Taq DNA polymerase*

\* developed and manufactured by Hoffmann-La Roche and commercially available from Perkin Elmer (Norwalk, Conn.).

Amplification reactions were carried out in a DNA Thermal Cycler 480, marketed by Perkin Elmer (Norwalk, Conn.), programmed for 32 amplification cycles (denature, anneal, and extend) followed by a final incubation (hold). To eliminate reagent evaporation, 2 drops of mineral oil were added to each reaction tube. The specific temperature cycling profile used is shown below.

| Thermal Cycling Times and Temperatures | | |
|---|---|---|
| 32 Cycles | denature | 60 seconds, 94° C. |
|  | anneal | 30 seconds, 60° C. |
|  | extend | 30 seconds, 72° C. |
| hold |  | 7 minutes, 72° C. |

Gel Electrophoretic Detection

Amplified DNA was detected by agarose gel electrophoresis to determine if amplification occurred. An agarose gel (100 ml of 3% NuSieve and 1.5% SeaChem) and 0.5 X TBE (0.045M Tris-borate and 0.001M disodium EDTA) running buffer were used. Ethidium bromide (0.5 µg/ml) was added to both the gel and the running buffer. Electrophoresis was carried out at 100 volts for approximately 1 hour. The gel was destained briefly in water and the ethidium bromide stained bands of DNA were visualized using UV irradiation.

The gel electrophoretic analysis confirmed the successful amplification of the target nucleic acid sequence from samples containing human genomic DNA.

EXAMPLE 2

Probe Hybridization Assay in Dot Blot Format

Probe hybridization was carried out in a dot blot format to detect the allele(s) present in samples of genomic nucleic acid. In the dot blot format, a small portion of the amplified nucleic acid was denatured, applied to a nylon filter, and immobilized as described below. The filter was then immersed in a solution containing labeled probe to allow hybridization to occur. Unbound probe was removed by washing under sequence-specific hybridization conditions, and the probes bound to the immobilized target nucleic acid were detected. Probes used in the hybridization were labeled with biotin as described in Levenson and Chang, 1989, in *Protocols: A Guide to Methods and Applications* (Innis et al., eds., Academic Press, San Diego), pages 92–112, incorporated herein by reference, to allow nonisotopic detection. The details of the assay are described below.

Detection Probes

Probes used to identify the allelic sequence variants present in the amplified ABO nucleic acid are described below. The particular nucleotides within the probe sequence which hybridize to a polymorphic site are shown underlined. Probes which hybridize to the nucleic acid strand shown in Table 1 are indicated with an asterisk; all other probes hybridize to the complement of the strand shown in Table 1. All probe oligonucleotides are shown in the 5' to 3' orientation.

The base pair present at the polymorphic site at position 29 of SEQ ID NO: 1 was identified using probes GZ26 (SEQ ID NO: 4) and GZ27 (SEQ ID NO: 5). The hybridizing regions of these probes also encompass polymorphic positions 32 and 33. Probe GZ26 (SEQ ID NO: 4) is specific for $O_1$ alleles, which have an A:T base pair at positions 29 and 32 and a C:G base pair at position 33. Probe GZ27 (SEQ ID NO: 5) is specific for $O_2$, A and $B_1$ alleles, which all have a G:C base pair at position 29, an A:T base pair at position 32, and a C:G base pair at position 33. Neither probe hybridizes to the $B_2$ allele, which has a G:C base pair at position 32, or to the $O_4$ allele, which has an T:A base pair at position 33.

GZ26 (SEQ ID NO: 4)   5'-AGCTCCAT<u>AT</u>G<u>A</u>CCGCAC

GZ27* (SEQ ID NO: 5)  5'-CGTGCG<u>GT</u>C<u>A</u>CATGGA

To distinguish O alleles from A and B alleles, probes were used which hybridize to a region of the ABO glycosyltransferase gene which encompasses the location of the additional G:C base pair which distinguishes the A and B alleles from the O alleles. Probe GZ29 (SEQ ID NO: 6) is specific for O alleles. Probe GZ30 (SEQ ID NO: 7) is specific for A and B alleles, which have an additional G:C base pair corresponding to a position between positions 77 and 78 of SEQ ID NO: 1.

GZ29 (SEQ ID NO: 6)   GGTACCCCTTGGCTGG

GZ30 (SEQ ID NO: 7)   GT<u>G</u>ACCCCTTGGCTGG

The nucleotide present at the polymorphic site at position 113 of SEQ ID NO: 1 was identified using probes GZ33 (SEQ ID NO: 8) and GZ34 (SEQ ID NO: 9). Probe GZ33 (SEQ ID NO: 8) is specific for $O_2$ and A alleles, which have an A:T base pair at position 113. Probe GZ34 (SEQ ID NO: 9) is specific for $O_1$, $O_3$, $O_4$, and B alleles, which have a G:C base pair at position 113.

GZ33 (SEQ ID NO: 8)   GGAGGGCAC<u>A</u>TTCAACAT

GZ34* (SEQ ID NO: 9)  GATGTTGAA<u>C</u>GTGCCCTC

Example 3, below, describes using the above set of six probes to classify alleles into a subset of the seven alleles described herein. All alleles were classified as $O_1$, $O_2$, A, or B alleles. At the time the genotyping described in example 3 was carried out, only the $O_1$, $O_2$, A, and B alleles had been observed. The existance of additional alleles was indicated by the occurrence of unexpected hybridization results. Subsequent sequencing led to the discovery of the polymorphism at position 32 which subdivides the B alleles, the polymorphism at position 33 which identifies the $O_4$ allele, and the combination of base pairs at positions 29 and 113, which identifies the $O_3$ allele. Because, the $B_2$, $O_3$, and $O_4$ alleles are relatively uncommon, it still might be desirable to classify alleles as $O_1$, $O_2$, A, or B alleles. If the polymorphisms at position 32 and 33 are not detected, the subtypes of the B alleles are not distinguished and the $O_4$ is not distinguished from the $O_1$ allele, but the $O_3$ allele is still distinct. Detecting only the polymorphisms at positions 29, 77–78 (deletion), and 113 by probe hybridization enables identification of all diploid genotypes with the exception that $O_3$.A and $O_2$.$B_1$ genotypes give identical hybridization results.

Genotyping wherein all seven alleles are distinguished can be carried out using, in addition to the probes described above, additional probes in order to identify the base pairs present at positions 32 and 33. Because of the proximity of the polymorphic sites at positions 29, 32, and 33, the base pairs present can be detected using probes which hybridize to a region encompassing positions 29–33 and which detect a specific pattern of base pairs present at positions 29, 32, and 33. Because all alleles contain one of four sequence variants within the region encompassing positions 29–33, four probes, each encompassing positions 29–33 and hybridizing to a distinct sequence variant, are sufficient to determine the base pairs present at positions 29, 32, and 33 in each allele. Probes GZ26 (SEQ ID NO: 4) and GZ27 (SEQ ID NO: 5), described above, detect two of the four sequence variants. Probe GZ26 (SEQ ID NO: 4) detects alleles which have an A:T base pair at positions 29 and 32 and a C:G base pair at position 33. Probe GZ27 (SEQ ID NO: 5) detects alleles which have a G:C base pair at position 29, an A:T base pair at position 32, and a C:G base pair at position 33. Probes P1 (SEQ ID NO 10) and P2 (SEQ ID NO 10), provided below, detect the other two sequence variants. Probe P1 (SEQ ID NO 10) detects alleles which have a A:T base pair at position 29, an A:T base pair at position 32, and a T:A base pair at position 33. Probe P2 (SEQ ID NO 10) detects alleles which have a G:C base pair at positions 29 and 32 and a C:G base pair at position 33. Used together, these four probes detect all combinations of base pairs present at positions 29, 32, and 33. Furthermore, the addition of P1 (SEQ ID NO 10) and P2 (SEQ ID NO 10) to the six-probe set described above enables genotyping all seven alleles.

P1   (SEQ ID NO: 10)   5'-AGCTCCATAT<u>GAT</u>CGCAC

P2   (SEQ ID NO: 11)   5'-AGCTCCAT<u>GT</u>G<u>GC</u>CGCAC

A set of probes designed to identify the base pair present at each of the five polymorphic sites can detect 27 of the 28 possible diploid genotypes. The $O_3$.A and $O_2$.$B_1$ genotypes are not distinguishable by detecting the base pair present at each polymorphic site independently. The ambiguity arises because the combined probe hybridization pattern does not indicate which allele contributes a particular base pair to the observed probe hybridization pattern. Both the $O_3$ and $O_2$ alleles and the A and $B_1$ alleles are distinguished only by the base pair present at position 113. Samples from $O_3$.A and $O_2$.$B_1$ genotypes contain both nucleic acid with a G:C at position 113 and nucleic acid with an A:T base pair at position 113. Distinguishing these genotypes requires determining which allele contributes, for example, the A:T base pair, which is not determined when the polymorphic sites are independently analyzed.

Genotyping ambiguity can be resolved using sequence-specific amplification to amplify only a subset of the alleles which could be present in the ambiguous sample. For example, sequence-specific amplification of nucleic acid from only A or B alleles using a primer specific for the additional G:C base pair that distinguishes the A and B alleles from the O alleles, followed by detection of the base pair at position 113, enables distinguishing A and B alleles. Amplifying only A or B alleles from samples known to be either an $O_3$.A or an $O_2$.$B_1$ genotype and identifying the amplified allele enables distinguishing $O_3$.A and $O_2$.$B_1$ genotypes. The use of sequence-specific amplification to eliminate genotyping ambiguity has been used in HLA DRB genotyping methods described in WO 92/10589, incorporated herein by reference.

Genotyping ambiguity can also be resolved by further detecting another polymorphic site outside the region of SEQ ID NO: 1. For example, Lee and Chang, 1992, supra, describe a polymorphic site at position 700 of the coding sequence which results in an Alu I site in B alleles not present in A alleles. The ability to distinguish A and B alleles enables distinguishing $O_3.A$ and $O_2.B_1$ genotypes.

Dot-Blot Assay

PCR products from amplification reactions carried out essentially as described in Example 1 were denatured by treatment with alkali. Specifically, 10 µl of PCR product was added to 90 µl of a denaturation solution consisting of 4.5 µl of 0.5M EDTA (pH 8.0), 7.2 µl of 5N NaOH, and 78.3 µl of $H_2O$. The mixture was incubated at room temperature for 10 minutes to complete denaturation.

BioDyne™ B nylon filters (Pall Corp., Glen Cove, N.Y.) were prepared by soaking in $H_2O$ for 5 to 10 minutes and further rinsing with 200 µl of $H_2O$ after the dot-blot manifold (Bio-Dot™ from Bio Rad, Richmond, Calif.) had been set up. The 100 µl denatured sample mixture was applied under vacuum to the nylon membrane using the dot blot apparatus. Each well was then rinsed with 200 µl of 0.4N NaOH, then rinsed briefly with 2X SSC, and air dried until no pools of liquid were left. The immobilized DNA was crosslinked to the nylon filter by ultraviolet irradiation at a flux of 500 mJ/cm² with a Stratalinker™ (Stratagene, La Jolla, Calif.) UV light box (at the "autocrosslink" setting).

Hybridization was carried out in hybridization buffer (5X SSPE, 0.5% SDS) containing 2 µM biotinylated probe. The filters were allowed to hybridize for 25–30 minutes at 55° C. After hybridization, filters were rinsed in a wash buffer (2.5X SSPE, 0.1% SDS) at room temperature to remove most of the excess probe.

The biotin probe labels were conjugated to horseradish peroxidase-streptavidin (HRP-SA) by incubating the filters in an enzyme conjugate solution containing hybridization buffer and HRP-SA. The enzyme conjugate solution was prepared by adding 8 µl of Enzyme Conjugate: HRP-SA from Perkin Elmer (Norwalk, Conn.) to each ml of hybridization solution. Each filter was incubated in the enzyme conjugate solution for 5 minutes at 55° C. Following conjugation, filters were rinsed in wash buffer at room temperature.

A stringent wash was carried out in wash buffer for 12 minutes at 55° C. in a shaking water bath. The sequence-specific hybridization conditions of the stringent wash ensured that only probes exactly complementary to the target sequence remained bound.

Biotinylated probes which remained bound to the immobilized amplification product were visualized as follows. A color development solution was prepared by mixing 100 ml of citrate buffer (0.1M Sodium Citrate, pH 5.0), 5 ml 3,3',5,5'-tetramethylbenzidine (TMB) solution (Perkin Elmer, Norwalk, Conn.), and 100 µl of 3% hydrogen peroxide. Filters were first rinsed in 100 mM sodium citrate (pH 5.0) for 5 minutes, then incubated in the color development solution with gentle agitation for 10 minutes at room temperature in the dark. The TMB, initially colorless, was converted by the probe-bound HRP, in the presence of hydrogen peroxide, into a colored precipitate. The developed filters were rinsed in water for several minutes and immediately photographed.

EXAMPLE 3

Frequencies of the ABO Alleles

To assess the frequency of ABO alleles, samples from 622 individuals from 4 different populations were typed at the ABO locus. The sampled populations consisted of 178 African Americans, 181 U.S. Caucasians, 174 U.S. Hispanics, and 89 Japanese, respectively.

Amplification of ABO nucleic acid was carried out essentially as described in Example 1, with the following exceptions. First, additional amplification primers specific for target sequences from 8 other genes were included in the amplification mixture so that target sequences from each gene were amplified simultaneously. Second, the final reagent concentrations were as follows:

2 ng purified human genomic DNA
200 nM each primer
200 µM of each dNTP
50 mM KCl
20 mM Tris-HCl, pH 8.3
3 mM $MgCl_2$.
1.5 µl of modified DNA polymerase solution (~7.5 units)

The modified DNA polymerase used was Taq DNA polymerase which had been reversibly inactivated by a reaction with a 200-fold molar excess of citraconic anhydride as described in copending U.S. patent application Ser. No. 60/002,673, filed Aug. 25, 1995, incorporated herein by reference. Following inactivation, amplifications were carried out using a dilution series of the modified enzyme to determine an amount of the citraconylated Taq DNA polymerase solution which would yield essentially the same results in an amplification as obtained using 7.5 units of unmodified Taq DNA polymerase. The amount of DNA polymerase activity used in the co-amplifications (7.5 units) was increased over the amount used in the single amplifications (2.5 units) to facilitate the increased DNA synthesis required in a co-amplification. Based on the empirical determination, 1.5 µl of the modified DNA polymerase solution were added to each reaction. The modified DNA polymerase was used in the co-amplifications in order to achieve a "hot-start", as described above. A pre-reaction incubation of the reaction mixture was carried out for 5 minutes, 30 seconds at 94° C. to reactivate the modified DNA polymerase.

The allele designations used herein are defined in Table 3, below, in terms of the polymorphism detected using the set of six probes described above. The positions of the polymorphic sites are numbered in reference to SEQ ID NO: 1. For each allele, the base pairs present at the polymorphic sites at positions 29 and 113, and the presence or absence of an additional G:C base pair between positions 77 and 78 of SEQ ID NO: 1, were determined. The bases pair present at positions 32 and 33, was not separately determined.

TABLE 3

ABO Glycosyltransferase Alleles

| Allele | Positions 29 | G:C? | Position 113 |
|---|---|---|---|
| $O_1$ | A:T | No | G:C |
| $O_2$ | G:C | No | A:T |
| A | G:C | Yes | A:T |
| B | G:C | Yes | G:C |

Allele identification was carried out as described in Example 2. The allele and genotype frequencies observed for each of the populations are given in the tables, below. Expected genotype frequencies were calculated from the observed allele frequencies assuming Hardy-Weinberg equilibrium.

As described above, the present genotyping was carried out prior to the discovery of the $B_2$, $O_3$, and $O_4$ alleles.

Unexpected results were observed from 13 African Americans, 4 U.S. Caucasians, 5 U.S. Hispanics, and 8 Japanese. The most frequently observed unexpected result was a failure of GZ27 (SEQ ID NO: 2), which was expected to hybridize to B alleles, to hybridize to a sample which was typed as $O_1,B$ based on the hybridization of the other five probes. Subsequent sequence analysis determined that these samples were actually $O_1,B_2$. Of the 30 samples which yielded unexpected hybridization results, 3 African American and 1 U.S. Hispanic samples yielded uninterpretable results and have been omitted from the results presented below. Allele and genotype frequencies were calculated using the 618 samples which provided interpretable hybridization results. In retrospect, in view of the subsequent discovery of the $O_3$ allele, a bias in the estimates of the frequencies of the A and B alleles was present because both $O_3,A$ and $O_2,B_1$ genotypes, which are indistinguishable using the present probe set, would have been classified as $O_2,B$ genotypes. Thus, the estimated frequency of the $O_2,B$ genotypes was an overestimate. However, because the $O_3$ allele is uncommon, it is likely that the occurrence of $O_3,A$ genotypes did not significantly affect the frequency estimates obtained.

TABLE 4

Allele Frequency

| Allele | U.S. Caucasian | African American | Hispanic | Japanese |
|---|---|---|---|---|
| $O_1$ | 0.265 | 0.297 | 0.402 | 0.298 |
| $O_2$ | 0.381 | 0.354 | 0.361 | 0.315 |
| A | 0.290 | 0.163 | 0.159 | 0.253 |
| B | 0.064 | 0.186 | 0.078 | 0.135 |

TABLE 5

ABO Genotype Distribution (African American)

| Genotype | Number Observed | Observed Frequency | Expected Frequency |
|---|---|---|---|
| $O_1,O_1$ | 13 | 0.074 | 0.088 |
| $O_1,O_2$ | 38 | 0.217 | 0.211 |
| $O_1,A$ | 18 | 0.103 | 0.097 |
| $O_1,B$ | 22 | 0.126 | 0.110 |
| $O_2,O_2$ | 21 | 0.120 | 0.126 |
| $O_2,A$ | 20 | 0.114 | 0.115 |
| $O_2,B$ | 24 | 0.137 | 0.132 |
| A,A | 4 | 0.023 | 0.027 |
| A,B | 11 | 0.063 | 0.060 |
| B,B | 4 | 0.023 | 0.034 |

TABLE 6

ABO Genotype Distribution (U.S. Caucasian)

| Genotype | Number Observed | Observed Frequency | Expected Frequency |
|---|---|---|---|
| $O_1,O_1$ | 6 | 0.033 | 0.070 |
| $O_1,O_2$ | 44 | 0.243 | 0.202 |
| $O_1,A$ | 31 | 0.171 | 0.154 |
| $O_1,B$ | 9 | 0.050 | 0.034 |
| $O_2,O_2$ | 22 | 0.122 | 0.145 |
| $O_2,A$ | 42 | 0.232 | 0.221 |
| $O_2,B$ | 8 | 0.044 | 0.048 |
| A,A | 13 | 0.072 | 0.084 |
| A,B | 6 | 0.033 | 0.037 |
| B,B | 0 | 0.000 | 0.004 |

TABLE 7

ABO Genotype Distribution (U.S. Hispanic)

| Genotype | Number Observed | Observed Frequency | Expected Frequency |
|---|---|---|---|
| $O_1,O_1$ | 24 | 0.139 | 0.161 |
| $O_1,O_2$ | 54 | 0.312 | 0.290 |
| $O_1,A$ | 29 | 0.168 | 0.128 |
| $O_1,B$ | 8 | 0.046 | 0.063 |
| $O_2,O_2$ | 21 | 0.121 | 0.131 |
| $O_2,A$ | 16 | 0.092 | 0.115 |
| $O_2,B$ | 13 | 0.075 | 0.056 |
| A,A | 3 | 0.017 | 0.025 |
| A,B | 4 | 0.023 | 0.025 |
| B,B | 1 | 0.006 | 0.006 |

TABLE 8

ABO Genotype Distribution (Japanese)

| Genotype | Number Observed | Observed Frequency | Expected Frequency |
|---|---|---|---|
| $O_1,O_1$ | 8 | 0.090 | 0.089 |
| $O_1,O_2$ | 16 | 0.180 | 0.187 |
| $O_1,A$ | 14 | 0.157 | 0.151 |
| $O_1,B$ | 7 | 0.079 | 0.080 |
| $O_2,O_2$ | 7 | 0.079 | 0.099 |
| $O_2,A$ | 17 | 0.191 | 0.159 |
| $O_2,B$ | 9 | 0.101 | 0.085 |
| A,A | 5 | 0.056 | 0.064 |
| A,B | 4 | 0.045 | 0.068 |
| B,B | 2 | 0.022 | 0.018 |

We claim:

1. An isolated oligonucleotide which consists of a subsequence of the intron sequence that is nucleotides 1 to 58 of SEQ ID NO: 1 and which comprises a nucleotide sequence at least about 10 nucleotides in length, wherein said nucleotide sequence is contained in the region consisting of positions 22–58 of SEQ ID NO: 1.

2. A DNA vector comprising said oligonucleotide of claim 1.

3. An isolated oligonucleotide about 15 to about 35 nucleotides in length exactly or substantially complementary to either strand of SEQ ID NO: 1 in a region which encompasses a polymorphic site selected from the polymorphic sites at nucleotide positions 29, 32, and 33, and wherein said oligonucleotide is exactly complementary to SEQ ID NO: 1 at said polymorphic site.

4. An isolated oligonucleotide of claim 3, wherein said region is about 15 to about 35 nucleotides in length.

5. An isolated oligonucleotide of claim 3 selected from the group consisting of GZ26 (SEQ ID NO: 4), GZ27 (SEQ ID NO: 5), P1 (SEQ ID NO: 10), P2 (SEQ ID NO: 11), and the exact complements thereof.

6. A kit for determining the genotype of an individual at the ABO glycosyltransferase locus comprising an oligonucleotide of claim 3.

7. A kit for determining the genotype of an individual at the ABO glycosyltransferase locus comprising an oligonucleotide of claim 4.

8. A kit for determining the genotype of an individual at the ABO glycosyltransferase locus comprising an oligonucleotide of claim 5.

9. A method for detecting the presence of a variant sequence of the ABO glycosyltranferase gene in a sample containing human nucleic acids comprising:

(a) mixing said nucleic acid with an oligonucleotide about 15 to about 35 nucleotides in length exactly or substantially complementary to either strand of SEQ ID NO: 1 in a region which encompasses a polymorphic site selected from the polymorphic sites at nucleotide positions 29, 32, and 33, wherein said oligonucleotide is exactly complementary to said variant sequence at said polymorphic site, under conditions wherein said oligonucleotide binds to said nucleic acid to form a stable hybrid duplex only if said nucleic acid contains said variant sequence; and (b) detecting the presence of any hybrids formed between said oligonucleotide and said nucleic acid, which indicates the presence of said variant sequence.

10. A method of claim 9, wherein, wherein said region is about 15 to about 35 nucleotides in length.

11. A method of claim 9, wherein said oligonucleotide is selected from the group consisting of GZ26 (SEQ ID NO: 4), GZ27 (SEQ ID NO: 5), P1 (SEQ ID NO: 10), P2 (SEQ ID NO: 11), and the exact complements thereof.

12. A method of claim 9, wherein said nucleic acid is amplified prior to step (a).

13. A method of claim 9, wherein said detecting in step (b) comprises carrying out a amplification reaction, using said oligonucleotide as an amplification primer, under conditions under which amplification occurs only if said oligonucleotide forms a stable hybrid duplex with said nucleic acid.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 161 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: exon
        ( B ) LOCATION: 59..161

( i x ) FEATURE:
        ( A ) NAME/KEY: intron
        ( B ) LOCATION: 1..58

( i x ) FEATURE:
        ( A ) NAME/KEY: CDS
        ( B ) LOCATION: 59..161
        ( D ) OTHER INFORMATION: /partial ( x i ) SEQUENCE DESCRIPTION: SEQ ID NO:1:

```
CATGTGGGTG GCACCCTGCC AGCTCCATRT GRYCGCACGC CTCTCTCCAT GTGCAGTAGG      60

AAGGATGTCC TCGTGGTACC CCTTGGCTGG CTCCATTGT  CTGGGAGGGC ACRTTCAACA     120

TCGACATCCT CAACGAGCAG TTCAGGCTCC AGAACACCAC C                         161
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
ATGTGGGTGG CACCCTGC                                                    18
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GGTGGTGTTC TGGAGCCTGA A                                                21
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGCTCCATAT GACCGCAC                                                                                          18

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGTGCGGTCA CATGGA                                                                                            16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGTACCCCTT GGCTGG                                                                                            16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTGACCCCTT GGCTGG                                                                                            16

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGAGGGCACA TTCAACAT                                                                                          18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GATGTTGAAC GTGCCCTC                                                                                          18

(2) INFORMATION FOR SEQ ID NO:10:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:10:

AGCTCCATAT GATCGCAC                                                                18

(2) INFORMATION FOR SEQ ID NO:11:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:11:

AGCTCCATGT GGCCGCAC                                                                18